(12) United States Patent
Kaplan et al.

(10) Patent No.: US 7,736,347 B2
(45) Date of Patent: Jun. 15, 2010

(54) METHODS AND APPARATUS FOR PERICARDIAL ACCESS

(75) Inventors: Aaron V. Kaplan, 851 Carnation Ct., Los Altos, CA (US) 94024; Jordan T. Bajor, Palo Alto, CA (US); Nubar S. Manoukian, Cupertino, CA (US)

(73) Assignee: Aaron V. Kaplan, Los Altos, CA (US)

( * ) Notice: Subject to any disclaimer, the term of this patent is extended or adjusted under 35 U.S.C. 154(b) by 279 days.

(21) Appl. No.: 11/873,228

(22) Filed: Oct. 16, 2007

(65) Prior Publication Data

US 2008/0108945 A1    May 8, 2008

Related U.S. Application Data

(60) Continuation of application No. 10/002,329, filed on Nov. 1, 2001, now Pat. No. 7,309,328, which is a division of application No. 09/397,392, filed on Sep. 16, 1999, now Pat. No. 6,423,051.

(51) Int. Cl.
*A61M 25/00* (2006.01)

(52) U.S. Cl. ...................................... 604/264

(58) Field of Classification Search ................. 604/264, 604/272, 275, 523, 174, 22, 164.01, 164.06, 604/165.04, 912, 164.11; 606/167, 170, 606/179, 180
See application file for complete search history.

(56) References Cited

U.S. PATENT DOCUMENTS

| 3,685,509 | A | * | 8/1972 | Bentall ........................ 600/583 |
| 4,164,943 | A | | 8/1979 | Hill et al. |
| 4,222,380 | A | * | 9/1980 | Terayama .................... 604/115 |
| 4,281,659 | A | | 8/1981 | Farrar et al. |
| 4,991,578 | A | | 2/1991 | Cohen |
| 4,995,866 | A | | 2/1991 | Amplatz et al. |
| 5,071,428 | A | | 12/1991 | Chin et al. |
| 5,226,890 | A | | 7/1993 | Ianniruberto et al. |
| 5,332,398 | A | | 7/1994 | Miller et al. |
| 5,407,427 | A | | 4/1995 | Zhu et al. |
| 5,695,504 | A | * | 12/1997 | Gifford et al. ............... 606/153 |
| 5,827,216 | A | | 10/1998 | Igo et al. |

* cited by examiner

*Primary Examiner*—Manuel A Mendez
(74) *Attorney, Agent, or Firm*—Hamre, Schumann, Mueller & Larson, P.C.

(57) ABSTRACT

An access tube is used for accessing an anatomic space, such as a pericardial space between the parietal and visceral pericardia. The access tube is advanced against the parietal pericardium and an anchor structure thereon embedded into the parietal pericardium. The access tube can then be used to separate the parietal and visceral pericardia and enlarge the pericardial space. After such enlargement, a needle or other access device can be introduced through the access tube into the pericardial space to provide access for a wide variety of purposes, including aspiration, infusion, and guidewire placement.

10 Claims, 4 Drawing Sheets

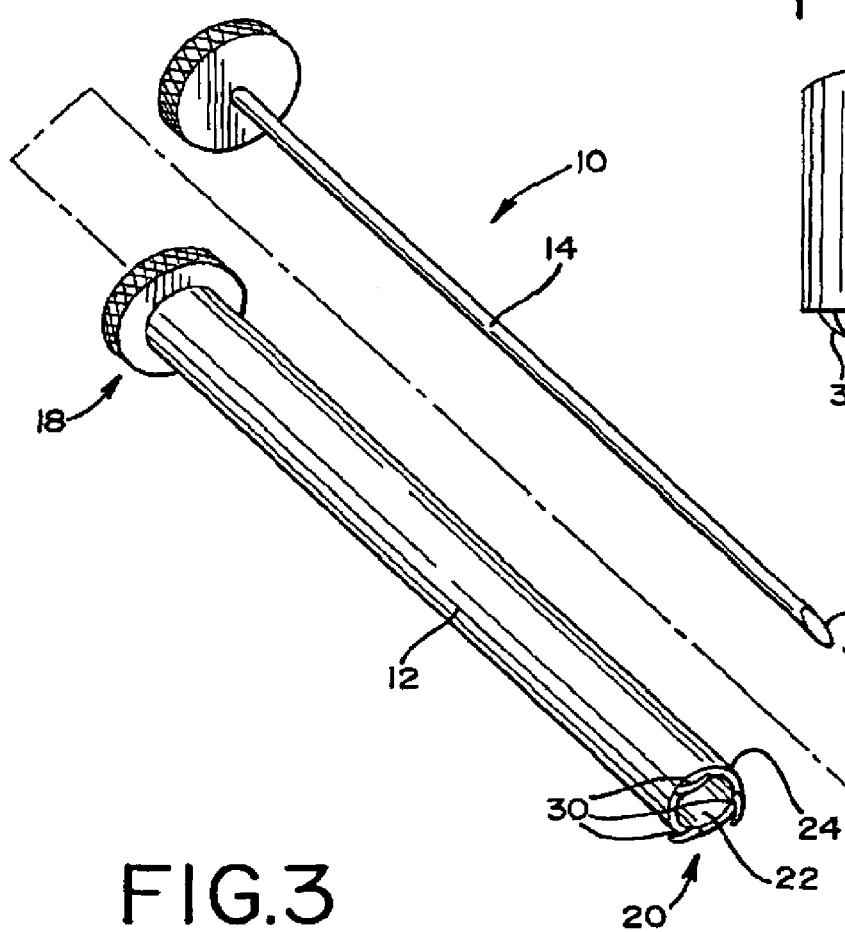
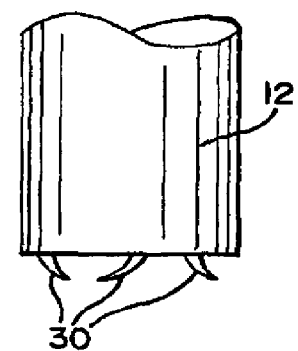
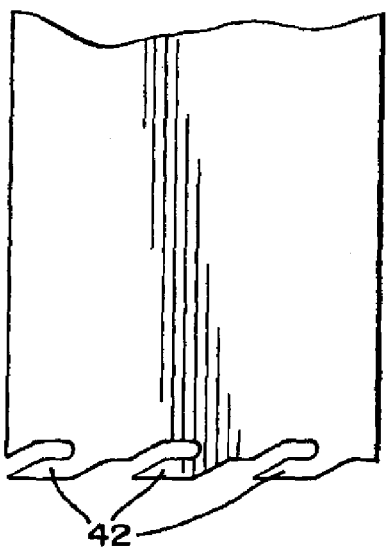
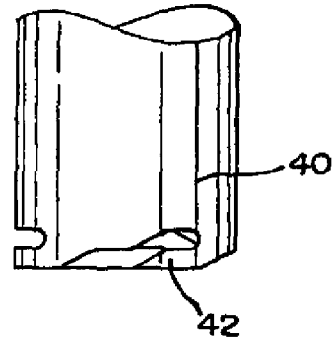

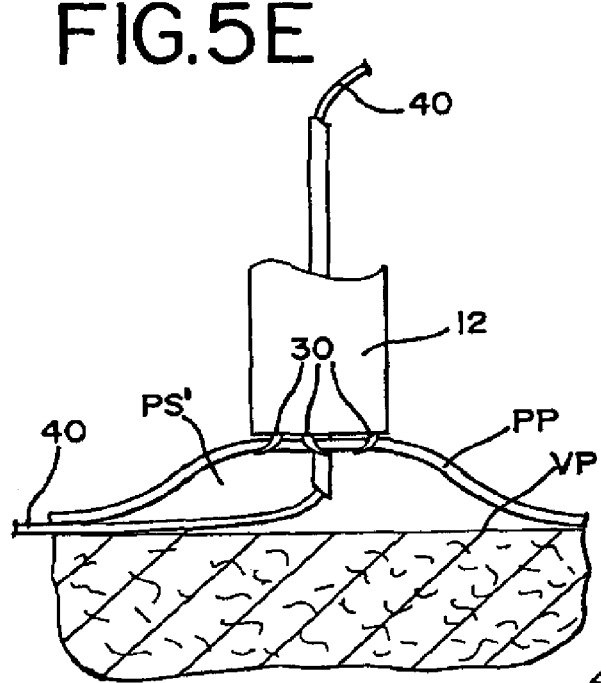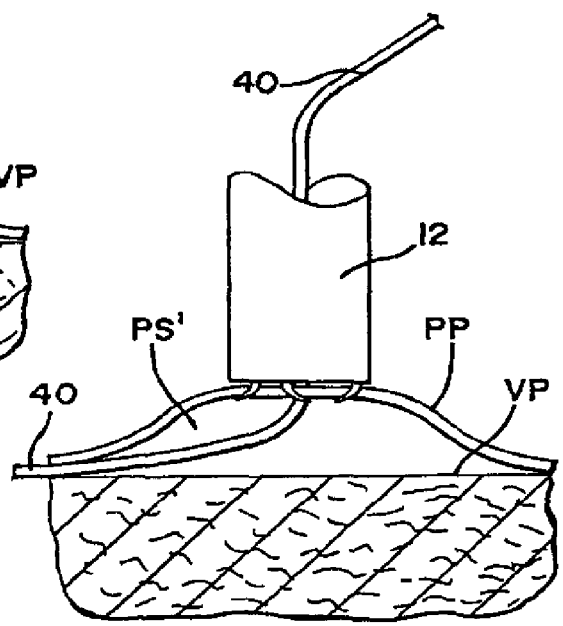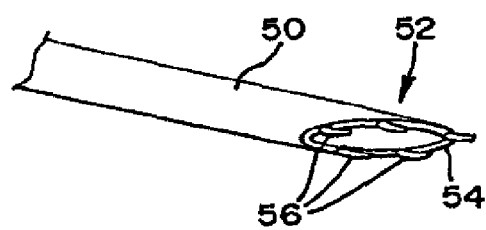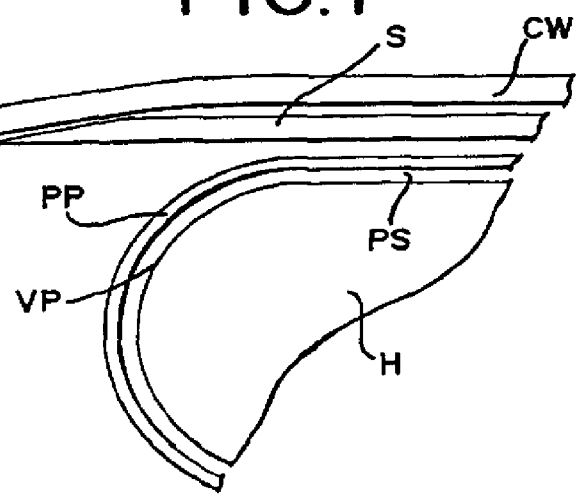

METHODS AND APPARATUS FOR PERICARDIAL ACCESS

This application is a continuation of Ser. No. 10/002,329, filed Nov. 1, 2001, now U.S. Pat. No. 7,309,328, which is a divisional of Ser. No. 09/397,392, filed Sep. 16, 1999, now U.S. Pat. No. 6,423,051, issued Jul. 23, 2002.

BACKGROUND OF THE INVENTION

1. Field of the Invention

The present invention relates generally to medical devices and methods. More particularly, the present invention relates to methods and devices for accessing the pericardial space in a minimally invasive manner.

The human heart is enveloped within a tissue structure referred to as the pericardium. The pericardium includes two major portions. The portion of the pericardium which lies immediately over the surface of the heart is referred to as the visceral pericardium. The second portion is formed as a sac around the visceral pericardium and is referred to as the parietal pericardium. Normally, the visceral and parietal pericardia lie in close contact with each other and are separated only by a thin layer pericardial fluid. The space (really more of a potential space) between the visceral and parietal pericardia is referred to as the pericardial space.

Access to the pericardial space can be necessary or beneficial under a variety of circumstances. Open surgical access van be obtained via open sternotomy where the patient's sternum is divided and the parietal pericardium is exposed. Alternatively, the pericardial space can be approached from a skin incision made below the xiphoid through which the parietal pericardium is identified. Such approaches, however, are highly traumatic, requiring general anesthesia and useful only under compelling circumstances. Access to the pericardial space can also be achieved using a thoracoscopic approach. Under general anesthesia, the left lung is deflated after which multiple holes are made for the thoracoscope and various instruments. The pericardium is then entered using standard videoscopic techniques. The thoracoscopic approach typically requires the placement of a chest tube and admission to the hospital for the initial 1-2 post-operative days.

In patients who require drainage of a large pericardial effusion, a simple percutaneous approach can be used. Through a small (2-4 mm) cutaneous incision between the xiphoid and costal cartilage, a spinal needle (18-20 gauge) is advanced in a superior/posterior fashion. At appropriate intervals, the stylet is removed and fluid aspiration is attempted. If no fluid is obtained, the stylet is replaced and the needle advanced again. This cycle is repeated until fluid is aspirated. If the needle is advanced too far, the heart can be punctured and is why a large pericardial effusion must be present on ensure adequate separation of the visceral and parietal pericardia.

A minimally invasive method for accessing the pericardial space is described in U.S. Pat. No. 5,827,216 to Igo et al. A pericardiocentesis apparatus is introduced via a subxiphoid approach to the heart. A vacuum is applied at a distal end of the device to form a "bleb," i.e., a locally expanded region in the pericardium. A needle can then be penetrated through the bleb, and the needle used for drawing fluids, delivering drugs, or the like. Although theoretically plausible, the ability to reliably maintain a seal against the pericardium can be problematic.

For these reasons, it would be desirable to provide additional and improved methods and apparatus for the minimally invasive access to a patient's pericardial space. The methods and devices should be suitable for a wide variety of minimally invasive approaches to the pericardium, including at least intercostal/transthoracic and subxiphoid approaches, and the like. The methods and devices should further provide for secure and stable capture of the parietal pericardium and permit the opening of a large space or volume between the parietal and visceral pericardia. Such access methods and apparatus should be useful for a wide variety of procedures to be performed in the pericardial space, including fluid withdrawal, drug delivery, diagnostic and therapeutic electrophysiology procedures, pacemaker lead implantation, defibrillator lead placement, transmysocardial revascularization, transmysocardial revascularization with drug delivery, placement of the left ventricular assist devices, placement of the arterial bypass graphs, in situ bypass, i.e., coronary artery-venous fistulae, placement of drug delivery depots, closure of the left arterial appendage, and the like. At least some of these objectives will be met by the invention described herein.

2. Description of the Background Art

U.S. Pat. No. 5,827,216, describes a pericardial access tube which draws a vacuum on the parietal pericardium as part of an access procedure, as discussed above. U.S. Pat. No. 5,071,428, describes a method for accessing the pericardial space for defibrillation lead implantation by grasping the parietal pericardium with forceps and cutting the pericardium with a scalpel. U.S. Pat. No. 4,281,659, describes a probe system having paired helical wires for securing the probe to a patient's skin. U.S. Pat. No. 4,164,943, describes a catheter anchor having multiple helical wires for securing the anchor to a patient's skin. U.S. Pat. No. 5,226,890, describes a trocar cannula anchor having a tapered thread for placement in a percutaneous tissue penetration. U.S. Pat. No. 5,332,398, describes and intramedullary catheter having a threaded end for implantation into a bone.

SUMMARY OF THE INVENTION

The present invention provides methods, apparatus, and kits for accessing an anatomic space having a wall with an outer surface. The wall may consist of a membrane, a capsule or the adventia, muscularis and endothelial layers of a hollow organ or vessel. The methods, apparatus, and kits are particularly useful for minimally invasive access procedures, but could also be used for accessing internal anatomic spaces where initial access to the wall of the outer surfaces achieved via open surgical or other techniques. The present invention will be particularly useful for accessing a patient's pericardial space for performing a wide variety of procedures generally as set forth above.

The phrase "anatomic space" is meant to include any natural, potential, or created space or cavity within a patient's body where it may be desirable to gain access for surgical, diagnostic, therapeutic, or any other purpose. Usually, the anatomic space will be within an organ or structure located beneath the patient's skin, such as the pericardial space which lies between the visceral and parietal pericardia, both of which lie beneath the chest wall and rib cage. Other internal organs which may be accessed include the intestines, fallopian tubes, gall bladder, kidneys, and the like.

Methods according to the present invention for accessing an anatomic space having a wall with an outer surface comprise embedding a distal end of an access tube into the outer surface. An access device, such as a stylet, needle, or other piercing instrument, may then be introduced through the access tube, penetrating the wall, and into the anatomic space while the access tube stabilizes the wall. Embedding the distal end of the access tube can be achieved in a wide variety of ways. Typically, an anchor structure at the distal end is engaged against the outer surface of the anatomic space wall and subsequently penetrated into the surface. For example, the anchor structure may comprise one or more penetrating points which are embedded into the wall by rotation of the access tube, distal advancement of the access tube, or the like. While the penetrating points will typically be fixed on the access tube, it will also be possible to provide spring-loaded or other selectively deployable penetrating points which can be embedded into the anatomic space wall while the access tube is held stationary. After the distal end of the access tube has been embedded into the anatomic space wall, the wall will usually be drawn or otherwise manipulated increasing the available access volume therein. In particular, by increasing the available volume, the risk of accidental injury from advancement of the access device into deep structures is significantly reduced. Increasing the access volume, however, can have other benefits. For example, it can improve the ability to image the anatomic space using a fiberoptic imaging scope, permit the introduction of various devices, drug delivery structures, or the like.

In preferred aspects of the present invention, the access device will be a hollow needle or stylet, and a guidewire will be positioned through the needle and into the anatomic space. The needle can then be withdrawn, and the guidewire used for access of a variety of diagnostic, therapeutic, or other catheters and devices.

In a further aspect of the method of the present invention, a pericardial space between the visceral and parietal pericardiums is accessed by percutaneously positioning a distal end of an access tube over the parietal pericardium. Positioning can be achieved either by a transthoracic or a subxiphoid approach beneath the sternum or from the abdominal cavity through the diaphragm, or the like. Once in position, a distal end of the access tube is embedded into the parietal pericardium in a manner which does not engage the visceral pericardium. The access tube is then drawn or otherwise manipulated to separate the parietal pericardium from the visceral pericardium to enlarge the available volume of the pericardial space therebetween. An access device, again usually a needle or hollow stylet, is then advanced through the access tube penetrating the parietal pericardium entering the pericardial space. Guidewires may then be positioned and a variety of particular protocols performed, generally as listed above.

The present invention still further provides systems comprising an access tube and a needle, stylet, or other equivalent device. The access tube has a distal end which can be selectively embedded into tissue, and the needle, stylet, or other access device has a lumen which is useful for subsequent placement of a guidewire, as generally described above. Optionally, the system may further comprise the guidewire capable of being positioned in the anatomic space through the needle.

The present invention still further provides kits for accessing the pericardial space of a patient. The kits comprise an access tube having a distal end which can be selectively embedded into tissue. Exemplary access tubes are described above. Kits will further comprise instructions for use according to any of the methods set forth above. Kits may optionally further comprise a package for holding at least the access tube and usually the instructions for use. Exemplary packages include boxes, trays, pouches, tubes, and the like. Usually, at least the access tube will be maintained sterilely within the package. Optionally, the needle, stylet, or other access device, may be included. Further optionally, the guidewires used for the methods of the present invention may also be included within the kit.

BRIEF DESCRIPTION OF THE DRAWINGS

FIG. 1 illustrates a system according to the present invention comprising an access tube and an access device in the form of a needle or stylet.

FIG. 2 is an enlarged view of the distal end of the access tube of FIG. 1.

FIGS. 3 and 4 illustrate an alternative construction of the access tube of the present invention.

FIGS. 5A-5F illustrate use of the system of FIG. 1 for accessing a pericardial space according to the method of the present invention.

FIG. 6 illustrates a further alternative access tube useful in the methods of the present invention.

FIG. 7 illustrates use of the access tube of FIG. 6 in accessing a pericardial space according to the methods of the present invention.

DESCRIPTION OF THE SPECIFIC EMBODIMENTS

Figure 5A:
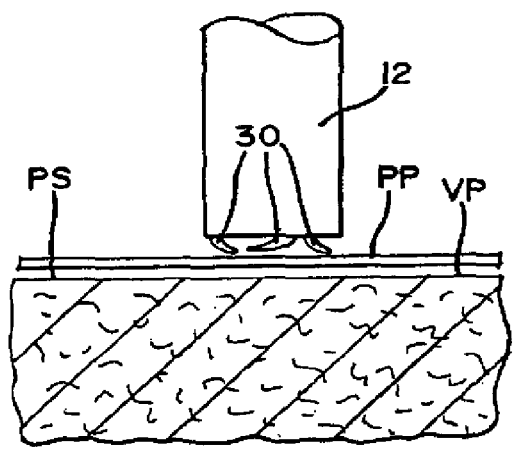

Systems according to the present invention include an access tube and an access device. The access tube engages and captures an outer surface of a wall which forms or surrounds the target anatomic space. In the exemplary case, the wall is the parietal pericardium which overlies the pericardial space over a patient's heart. The access device, in turn, is intended to pass through the access tube and to penetrate through the anatomic space wall and into the interior volume of the anatomic space. Using the access tube to first capture and stabilize the wall of the anatomic space facilitates introduction of the access device through the wall.

The access tube may have a wide variety of specific structures, but will generally be elongate, typically having a length in the range from 10 cm to 30 cm, more usually from 18 cm to 24 cm, and a relatively narrow maximum width, usually having a diameter in the range from 3 mm to 20 mm, more usually from 4 mm to 10 mm, and will have an anchor structure at its distal end in order to selectively engage and capture the outer surface of the anatomic space wall. The access tube allows for introduction of the access device through the target region of the anatomic space wall which is being held by the access tube. Most simply, the access tube is a tubular or cylindrical structure (usually but not necessarily having a continuous side wall without perforations) with the anchor structure disposed over a distal end thereof. Thus, the access device may simply be introduced through the central lumen or passage of the access tube so that it passes out through the anchor structure at the distal end of the device. Thus, when the anchor structure is engaging tissue, the access tube will necessarily pass through that region of tissue which is being held and stabilized by the distal end of the access tube. The ability to provide such peripheral engagement and stabilization of the anatomic space wall while the access tube is passed therethrough is a particular advantage of the present invention.

The access device may also have a wide variety of specific forms, but will usually be in the form of a needle, stylet, or other elongate structure having a sharpened distal tip for passage through the tissue of the anatomic space wall. Usually, the access device will also have a central lumen to permit introduction of a guidewire, infusion or aspiration of fluids, placement of leads or other implantable devices, or the like. Placement of a guidewire within the anatomic space may further provide for introduction of a wide variety of other diagnostic and therapeutic catheters and devices. The access device will typically be longer than the access tube so that it may be passed therethrough, usually having a length in the range from 12 cm to 35 cm, more usually from 20 cm to 26 cm. The maximum width or diameter of the access device will permit its introduction through the access tube, usually being the range from 0.2 mm to 2.0 mm, preferably from 0.4 mm to 0.8 mm.

The exemplary access tube and access device described below are relatively simple in construction. It will be appreciated that the construction could be varied in a number of ways for a variety of purposes. For example, the tubular structures of the access tube and/or the access device could be non-linear, telescoping, perforated, or have many other configurations. Additional features, such as additional lumens, imaging capabilities, pneumostatic valves, and the like, could also be added within the scope of the present invention.

Referring now to FIGS. 1 and 2, a first exemplary anatomic space access system 10 according to the present invention will be described. This system is particularly intended for access to a pericardial space, as will be described in more detail below. System 10 comprises an access tube 12 and an access device 14 in the form of a hollow needle or stylet having a sharpened distal end 16. The access tube 12 comprises a tubular body having a proximal end 18 and a distal end 20. The distal end 20 is simply an open port 22 having an annular surface 24. A plurality of tissue-penetrating elements 30 are disposed about the annular surface 24 and are oriented so that they may be engaged against a tissue surface and penetrated into that surface by rotation of the access tube 12 about its central access. The dimensions of the access tube 12 and access device 14 are generally within the ranges set forth above, and the tissue-penetrating elements will typically have a length (measured axially from the annular surface 24) in the range from about 0.5 mm to 3.0 mm, and will further be oriented at an angle in the range from 5° to 60° so that they penetrate into tissue as the tube 12 is rotated about its central axis.

The access tube 12 of FIGS. 1 and 2 is fabricated by attaching separate tissue-penetrating elements 30, typically short conical or horn-shaped needles, to the annular surface 24 of the body of the access tube. For mass production, it may be desirable to more simply form the tissue-penetrating elements at the distal end of the access tube. As illustrated in FIGS. 3 and 4, an access tube 40 having three penetrating elements 42 at its distal end may be formed from a flat sheet of material, typically metal, by forming the elements 42 into the flat sheet prior to rolling the sheet to form the tube. For metals, the elements may be formed by cutting, etching, abrasion, or any conventional metal-working technique. The flat sheet may be rolled and then closed over the mating longitudinal edges, typically by welding, or other conventional techniques.

Figure 5B:
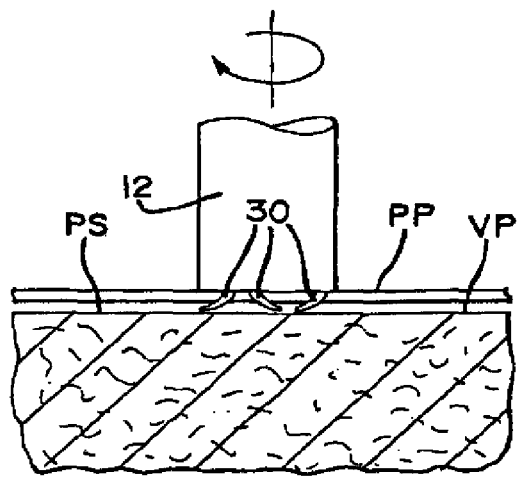
Figure 5C:
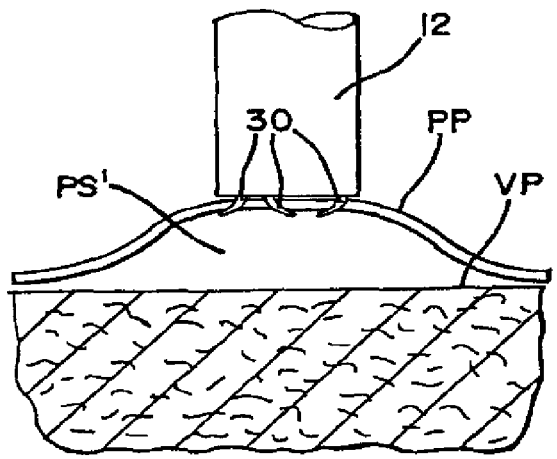
Figure 5D:
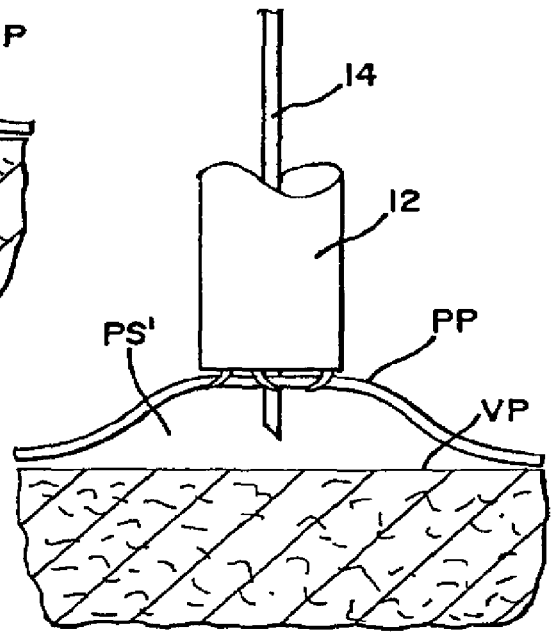

Referring to FIGS. 5A-5F, use of the access tube 12 and access device 14 for accessing a pericardial space PS of a patient will be described. The pericardial space PS is formed between the visceral pericardium VP and the parietal pericardium PP, as seen in FIG. 5A. The distal end of the access tube 12 can be introduced over the surface of the parietal pericardium PP, typically via a subxiphoid approach. After reaching the parietal pericardial surface, penetrating elements 30 may be engaged against the parietal pericardium and embedded therein by rotating the access tube 12 about its central axis, as illustrated in FIG. 5B. The penetrating elements 30 engage the parietal pericardium, but do not engage or advance into the visceral pericardium or structures below. Thus, once engaged, the access tube 12 is able to draw the parietal pericardium away from the visceral pericardium to create an enlarged pericardial space PS', as shown in FIG. 5C. After drawing the parietal pericardium PP, the access device 14 may be introduced through the access tube 12 and into the enlarged pericardial space PS', as shown in FIG. 5D. The access device 14 is then available to perform a wide variety of tasks and protocols. For example, it could be used for infusion or aspiration of fluids, drug delivery, diagnostic and therapeutic electrophysiology procedures, pacemaker lead implantation, defibrillator lead placement, transmysocardial revascularization, transmysocardial revascularization with drug delivery, placement of left ventricular assist devices, placement of arterial bypass graphs, in situ bypass, i.e., coronary artery-venous fistulae, placement of drug delivery depots, closure of the left atrial appendage, or the like.

In the exemplary embodiment of the present invention, the access device 14 will be used to introduce a guidewire 40 into the enlarged pericardial space PS', as shown in FIG. 5E. Once the guidewire 40 is in place, the access device 14 may be withdrawn, leaving the guidewire passing through the access tube 12, as illustrated in FIG. 5F. The guidewire 40 may then be used to introduce a wide variety of catheters or other diagnostic or therapeutic devices in order to perform any of the procedures listed above. In a preferred use, the guidewire 40 will be used to introduce a catheter and related instruments for closing the left atrial appendage, as generally described in U.S. application Ser. No. 09/315,601, filed May 20, 1999, now U.S. Pat. No. 6,488,689, the full disclosure of which is incorporated herein by reference.

The system of FIGS. 1 and 2 is particularly useful for engaging outer surface of the anatomic space walls in a generally perpendicular direction, allowing the penetrating elements to engage and capture the underlying tissue. In some instances, it may be desirable to provide systems intended to approach a tissue surface in a non-perpendicular direction. As illustrated in FIG. 6, an access tube 50 can be provided with a cylindrical body and an angled or chamfered distal end 52. An annular surface 54 at the distal end 52 can be provided with a plurality of fixed, generally axially aligned penetrating elements 56. Such elements will be able to engage tissue as the access tube 50 is advanced in a distal direction, allowing the tissue surface to be captured at oblique angles.

As illustrated in FIG. 7, the access tube 50 can be used to access a pericardial space PS from a subxiphoid approach. A patient's heart H underlies the sternum S beneath the chest wall CW, as illustrated in FIG. 7. The access tube 50 can be introduced beneath the inferior end of the sternum S to approach the parietal pericardium PP. The penetrating elements 56 can thus engage the parietal pericardium and draw it away from the visceral pericardium VP, similarly as shown in FIGS. 5A-5D. The access device 14 can then be introduced through the access tube 50 and into the enlarged pericardial space PS. The access device 14 can be used for introducing a guidewire or any of the other purposes described above.

Figure 8:
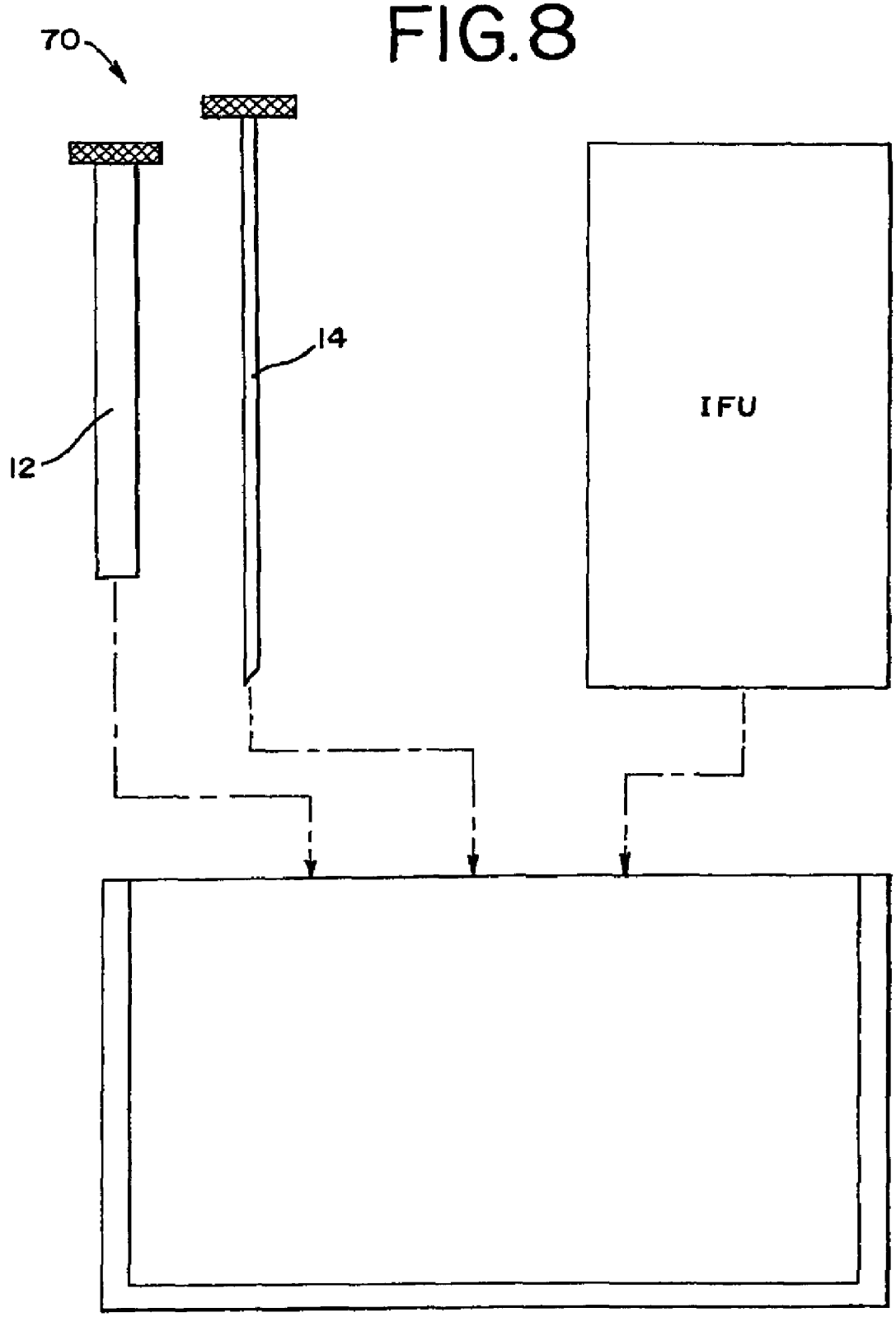
FIG. 8 illustrates a kit constructed in accordance with the principles of the present invention.

Referring now to FIG. 8, a kit 70 according to the present invention comprises at least an access tube (illustrated as access tube 12) and instructions for use (IFU) setting forth a method according to the present invention for accessing an anatomic space. Optionally, the kit may further include an access device, such as access device 14 described above, as well as packaging, typically in the form of a box, pouch, tray, tube, or the like. The kit 70 could further include a guidewire and other components or instruments useful for positioning the access tube and access device in performing the access methods. Instructions for use will usually be printed on a separate sheet of paper in the form of a package insert, but could also be printed partly or wholly on the packaging itself.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for accessing an anatomic space having a wall, said system comprising:
    an access tube having a distal end which can be selectively engaged at an outer side of the wall;
    a penetrating structure disposed proximate the distal end of the access tube, the penetrating structure being adapted for penetrating the outer side of the wall and through an inner side of the wall, the penetrating structure being configured to engage the inner side of the wall, such that when the penetrating structure engages the inner side of the wall and the distal end of the access tube is moved, the system is configured to cause corresponding enlargement of the anatomic space; and
    an access device having a lumen therethrough, said access device being configured to pass through the access tube and penetrate into the anatomic space when the access tube is engaged with the outer side of the wall of the anatomic space and when the penetrating structure is engaged with the inner side of the wall of the anatomic space.

2. A system as in claim 1, wherein the penetrating structure comprises an anchor structure proximate the distal end of the access tube.

3. A system as in claim 2, wherein the anchor structure comprises one or more penetrating elements.

4. A system as in claim 3, wherein the penetrating elements are inclined so as to be configured to penetrate into tissue when the access tube is rotated about its long axis.

5. A system as in claim 1, wherein the penetrating structure is adapted for engagement with the inner side of the wall so as to be engaged underneath the wall.

6. A system as in claim 1, further comprising a guidewire configured to be positioned into the anatomic space through the access device.

7. A system as in claim 1, wherein the access device is a needle.

8. A system for accessing the pericardial space between the visceral pericardium and parietal pericardium, said system comprising:
    an access tube having a distal end which can be selectively engaged at an outer side of the parietal pericardium;
    a penetrating structure disposed proximate the distal end of the access tube, the penetrating structure being adapted for penetrating the outer side of the parietal pericardium and through an inner side of the parietal pericardium, the penetrating structure being configured to engage the inner side of the parietal pericardium, such that when the penetrating structure engages the parietal pericardium and the distal end of the access tube is moved, the system is configured to cause corresponding enlargement of the pericardial space; and
    an access device, said access device being configured to pass through the access tube and penetrate into the pericardial space when the access tube is engaged with the outer side of the parietal pericardium and when the penetrating structure is engaged with the inner side of the parietal pericardium.

9. An apparatus for enlarging the pericardial space between the visceral pericardium and parietal pericardium, said apparatus comprising:
    an access tube having a distal end which can be selectively engaged at an outer side of the parietal pericardium; and
    a penetrating structure disposed proximate the distal end of the access tube, the penetrating structure being adapted for penetrating the outer side of the parietal pericardium and through an inner side of the parietal pericardium, the penetrating structure being configured to engage the inner side of the parietal pericardium, such that when the penetrating structure engages the parietal pericardium and the distal end of the access tube is moved, the system is configured to cause corresponding enlargement of the pericardial space.

10. The apparatus as in claim 9, wherein the penetrating structure comprises an anchor structure proximate the distal end of the access tube and the anchor structure comprises one or more penetrating elements.

* * * * *